(12) United States Patent
Koenig

(10) Patent No.: US 6,962,701 B2
(45) Date of Patent: Nov. 8, 2005

(54) METHODS OF PRIMING THE IMMUNOGENIC ACTIVITY OF VACCINES USEFUL FOR ELICITING A PROTECTIVE IMMUNE RESPONSE

(75) Inventor: Scott Koenig, Rockville, MD (US)

(73) Assignee: Medimmune, Inc., Gaithersburg, MD (US)

( * ) Notice: Subject to any disclaimer, the term of this patent is extended or adjusted under 35 U.S.C. 154(b) by 123 days.

(21) Appl. No.: 10/409,822

(22) Filed: Apr. 9, 2003

(65) Prior Publication Data

US 2003/0206907 A1 Nov. 6, 2003

Related U.S. Application Data

(63) Continuation of application No. 09/797,760, filed on Mar. 2, 2001, now Pat. No. 6,565,849.
(60) Provisional application No. 60/186,566, filed on Mar. 2, 2000.

(51) Int. Cl.$^7$ .............................................. A61K 39/395
(52) U.S. Cl. .............................. 424/130.1; 424/136.1; 424/178.1; 424/182.1; 424/193.1
(58) Field of Search .......................... 424/130.1, 138.1, 424/178.1–183.1, 193.1, 136.1

(56) References Cited

U.S. PATENT DOCUMENTS 5,824,307 A 10/1998 Johnson

FOREIGN PATENT DOCUMENTS

WO WO 99/61065 12/1999

OTHER PUBLICATIONS

Byers "What Can Randomized Controlled Trials Tell Us About Nutrition and Cancer Prevention?", CA Journal, vol. 49, No. 6, (Nov./Dec. 1999), pp. 353–361.*

Bellone et al. "Cancer immunotherapy: synthetic and natural peptides in the balance", Immunology Today, vol. 20, No. 10 (1999), pp. 467–462.*
Gura, "Systems for Identifying New Drugs Are Often Faulty", Science, vol. 278 (Nov. 1997), pp. 1041–1042.*
Riffkin et al. AA single amino–acid change between the antigenically different extracellular serine proteases V2 and B2 from Dichelobacter nodosus@, Gene, vol. 167 (1995), pp. 279–283.*
Abaza et al. AEffects of amino acid substitutions outside an antigenic site on protein binding to monoclonal antibodies of predetermined specificity obtained by peptide immunization@, Journal of Protein Chemistry, vol. 11, No. 5, (1992), pp 433–444.*
Cruse et al. Illustrated Dictionary of Immunology (Boca Raton, FL, CRC Press, Inc., 1995), p. 309. QR180.4.C78.*
Paul, Fundamental Immunology, (Philadelphia & New York, Lippincott–Raven Publishers, 1993), pp. 250 and 1311–1312. QR181.F84.*
Peter Seiler, et al, Induction of Protective Cytotoxc T Cell Responses in the Presence of High Titers of Virus–Neutralizing Antibodies: Implications for Passive and Active Imuunization, J. Exp. Med., The Rockfeller University Press, vol 187, No. 4, 649–654, Feb. 16, 1998.
James E. Crowe, Jr., et al. Cold–passaged, temperature–sensitive mutants of human respiratory syncytial virus (RSV) are highly attenuated, immunogenic, and protective in seronegative chimpanzees, even when RSV antibodies are infused shortly before immunization, Respiratory Viruses Section, Laboratory of Infectious Diseases, Vaccine 1995 vol. 13 No. 9 Dec. 5, 1994.

* cited by examiner

Primary Examiner—Jeffrey Stucker
(74) Attorney, Agent, or Firm—Medimmune, Inc.

(57) ABSTRACT

Disclosed are methods for vaccine priming, using co-treatment, at a temporally similar or at a previous time, with a priming antibody capable of priming, or enhancing, or potentiating the effects of a vaccine, or vaccine composition. Also disclosed are methods of using this process to prevent or treat disease.

13 Claims, No Drawings

METHODS OF PRIMING THE IMMUNOGENIC ACTIVITY OF VACCINES USEFUL FOR ELICITING A PROTECTIVE IMMUNE RESPONSE

This application is a continuation of U.S. Ser. No. 09/797,760, filed 2 Mar. 2001, now U.S. Pat. No. 6,565,849, which claims priority of U.S. Provisional Application Ser. No. 60/186,566, filed 2 Mar. 2000, the disclosures of which are hereby incorporated by reference in their entirety.

FIELD OF THE INVENTION

The present invention relates to a method of priming, enhancing and/or potentiating the effects of a vaccine using pretreatment with an antibody, including antibodies specific for the antigenic determinants from which the vaccine is derived.

BACKGROUND OF THE INVENTION

The use of vaccines and vaccine compositions is presently a major method of dealing with the prevention and treatment of disease. However, because such vaccines and vaccine compositions incorporate whole proteins or polynucleotides or active fragments thereof, the effectiveness of such treatments can be highly variable. In some cases, highly purified proteins and polypeptides, and fragments thereof, incorporating antigenic determinants characteristic of a microorganism, such as a virus or bacterium, may fail to show sufficiently active protection against infection by said organism, possibly because of structural or steric shortcomings in the particular polypeptide or fragments used as the basis for the vaccine. Consequently, attempts have been made to enhance the effectiveness of such vaccines by addition of potentiating agents to the treatment process, especially in cases such as the treatment of a cancer where said cancer may show unexpectedly high sensitivity to the potentiating agent.

Heretofore, many different procedures have been developed to enhance the activity of vaccines and vaccine compositions by increasing the immunogenicity of such compositions. Part of the problem with such measures has been the hit or miss character of these procedures, many of which are based on just trial and error and are not otherwise carefully calculated to elicit the type of response desired and which makes the vaccine worthwhile. Among the more effective procedures has been the use of adjuvants (such as Freund's complete adjuvant, although the latter is not useful in treating human patients) as well as the addition of simple organic molecules to the vaccine composition.

Many attempts at enhancing the immunogenicity of vaccines have revolved around extensive searches for small organic molecules that are effective, relatively non-toxic and economically advantageous to synthesize and utilize. Such efforts have met with only spotty success. Such compounds must, of course, be able to mimic the response with more complex immunogens, such as lipopolysaccharide of *Escherichia coli* and whole polypeptides used in immunogenic compositions. Some agents have shown promise, for example, the anti-tumor agent of U.S. Pat. No. 5,958,980.

Other approaches have involved forming particulate matter, such as by heat-induced aggregation of soluble antigens or by using self-aggregating antigenic particles (for example, the soluble antigen of hepatitis B virus possesses self-aggregation properties). Such particles have been found more useful in attracting immune cells such as macrophages and inducing immunity in the organism. Other attempts have employed more exotic structures such as liposomes, oily droplets, and alum precipitation.

Other methods of enhancing immunogenic activity of vaccines have included attempts to elicit an immunological reaction against an antigen administered along with a highly potent vaccine such that the latter provides a kind of adjuvant effect. For example, if a potent immunogen like killed *Bordetella pertussis* is administered along with a purified protein or polypeptide, the result is often a stronger immunogenic reaction to the purified protein or polypeptide, possibly due to the fact that the potent immunogen greatly stimulates the production of lymphokines, such as interleukin 4, that possess inter alia strong polyclonal activating activities.

Other methods have included such processes as slowing down the release of the immunogen so as to avoid activating suppressor pathways or avoiding direct intravenous administration, including subcutaneous devices to slowly release antigen.

Some methods have resorted to genetically engineering the organisms against which the immunogenic response is to be directed. For example, the vaccinia virus genome has been engineered to incorporate genes for various antigens of different pathogens. [See: Panicali and Paoletti, *Proc. Natl. Acad. Sci USA,* 79:4927 (1982); Smith et al, *Nature,* 302:490 (1983); Langford et al, *Mol. Cell Biol.,* 6:3191 (1986); also see U.S. Pat. No. 5,879,685 for a highly descriptive survey of past methodologies] Other approaches have employed the use of surface active agents (such as saponin).

However, all of these methods have proven less than completely satisfactory because each has one or more disadvantages, mostly having to do with the eliciting of unwanted side reactions involving the stimulation of biological pathways within the recipient organism that can have a negative effect on the overall efficacy of the method being used. For example, alum precipitation often shows unwanted inflammatory effects. In addition, co-administration of antigen along with a potent immunogen is often useful only for a limited number of small peptides. Further, genetically engineering potentially dangerous microorganisms necessarily engenders safety concerns.

The present invention avoids these disadvantages by providing a means of potentiating, or enhancing, or priming the immunogenic effects of a vaccine, or vaccine composition, by utilizing a pretreatment step involving a highly specific and high affinity neutralizing antibody to prime the immunogenic reaction and thereby potentiate the effects of subsequent administration of the appropriate vaccine, or vaccine composition.

BRIEF SUMMARY OF THE INVENTION

The present invention relates to a process for potentiating the immunogenic reaction of a given vaccine through pretreatment of an organism, such as a human patient, with a therapeutically effective amount of an antibody to prime response to the vaccine.

It is thus an object of the present invention to provide a method for enhancing the immunogenic activity of a vaccine, or vaccine composition, by first administering to an animal, such as a human patient, a therapeutically effective amount or dose of an antibody specific for an antigenic determinant of a cell or microorganism against which said animal is to be immunized, followed by administration to the same animal of an effective amount, or dose, of a vaccine, or vaccine composition, comprising at least one antigenic determinant for which the earlier administered antibody is specific.

It is another object of the present invention to provide a means of priming, or enhancing, or potentiating, the immunogenic activity of vaccines, and vaccine compositions, useful in immunizing against microorganisms, especially bacteria and viruses.

It is a further object of the present invention to provide a method for priming, enhancing or potentiating the immunogenic activity of vaccines, and vaccine compositions, useful in treating, and or preventing, diseases, especially where said disease afflicts a human patient, or where said human is at risk of contracting said disease. Among the diseases to be prevented or treated are those caused by bacteria and viruses, as well as chronic diseases, such as cancer.

DETAILED SUMMARY OF THE INVENTION

The present invention relates to a process for priming, or enhancing, or potentiating, all of which are considered synonymous when applied to the process of the present invention, an immunological response, whereby an animal is first treated by administration of a sample of an antibody followed at some finite time later by the administration to the same animal of a sample of a vaccine, or vaccine composition, whose immunogenic activity is to be primed, enhanced, or potentiated.

In accordance with the disclosure herein, the present invention relates to a process for priming, enhancing, or potentiating immunogenic activity such as in response to a vaccine, or vaccine composition, comprising:

(a) administering to an animal in need thereof an effective amount of an antibody specific for one or more of the antigenic determinants characteristic of said vaccine, or vaccine composition; and (b) administering to said animal an effective amount of said vaccine, or vaccine composition.

In accordance with the present invention, this process for priming the immunogenic activity of the vaccine, or vaccine composition, may involve administering the antibody at some point in time prior to administration of the vaccine, or vaccine composition, whose immunogenic activity is to be primed, enhanced or potentiated. Thus, the antibody may be administered an hour, or a few hours, prior to the administration of the vaccine, or vaccine composition, or said antibody may be administered up to 24 hours prior to said vaccine, or vaccine composition, or said antibody may be administered up to 48 hours, or up to 72 hours, or even up to a week, or even longer, prior to administration of said vaccine, or vaccine composition. The antibody and the vaccine, or vaccine composition, whose immunogenic activity is to be primed, enhanced or potentiated may also be administered simultaneously, either separately or as part of the same composition, or may even be administered only a few minutes apart. In addition, the vaccine, or vaccine composition, may even be administered just prior to administration of the antibody, possible up to several hours or even a day prior thereto. In applying the methods disclosed herein, it should be borne in mind that the object of said invention is to have the antibody and vaccine, or vaccine composition, work in sequence to achieve the desired priming, enhancing or potentiating of the underlying immunogenic effect.

As used herein, the term "priming" in its narrowest sense is synonymous with the terms "enhancing" and "potentiating" and refers to any form of increase in the immunogenic activity of a vaccine, or vaccine composition, as a result of administering to an animal, such as a human, a therapeutically effective dose of an antibody wherein said antibody is administered at any time prior to, simultaneous with, or just after administration to the same animal of an effective dosage of a vaccine, or vaccine composition, and wherein the antibody is specific for at least one antigenic determinant characteristic of the active epitopes present in said vaccine, or vaccine composition.

The present invention is also directed to a process in which either the antibody or the vaccine, or vaccine composition, represents a less than therapeutically effective dose of the respective antibody or vaccine, or vaccine composition, but together, as a result of the priming process, result in therapeutically effective action in treating the condition to be ameliorated, whether this be a disease caused by infection, or due to cancer, or some toxic effect due to the exposure of the patient to one or more toxins. Also in accordance with the present invention, both the antibody and the vaccine, or vaccine composition, may be administered at a less than therapeutically effective dose but, because of the priming effect, such combination results in effective therapy. Likewise, the antibody and/or the vaccine, or vaccine composition, according to the present invention may be administered in one or more (i.e., in a series) of doses, each of which is not by itself therapeutically effective to treat the subject condition or malady, but which in total, because of the priming effect, result in therapeutically effective treatment of said condition or malady. The advantage of such a schedule of administration might be, inter alia, potentially toxic effects of the antibody, vaccine, or both when given in doses therapeutically effective without the priming effect. Thus, in accordance with the present invention, such priming has the advantage of achieving a therapeutically, or prophylactically, effective dosage of either the antibody, or vaccine, or both, but with reduced, or absent, toxic effects.

In accordance with the disclosure herein, the term "priming" includes enhancement of a normal immune function, such as an immunogenic reaction, as well as the restoration of a depressed immune reaction, such as where the immunogenic activity of the vaccine, or vaccine composition, is either inadequate to be of genuine clinical value or else is simply reduced in effect, or is considered adequate for clinical use but is susceptible to enhancement, or increase, in activity. Consequently, the antibody, or antibodies, used according to the present invention are essentially co-stimulatory agents, or immunopotentiating agents, with respect to the vaccine, or vaccine composition, employed in the claims hereof.

Also in accordance with the present invention, there are provided vaccines, and vaccine compositions, for use herein. Such vaccines comprise immunogens that themselves may include proteins, nucleic acids, and active fragments thereof, the only real requirement being the ability of such substances to elicit an immunogenic response when introduced into an animal, especially a human.

The term "active fragment" means a fragment that generates an immune response (i.e., has immunogenic activity) when administered, alone or optionally with a suitable adjuvant, to an animal, such as a mammal, for example, a rabbit or a mouse, and also including a human.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to a polynucleotides, such terms refer to the products produced by treatment of said polynucleotides with any of the common endonucleases.

In accordance with a further aspect of the invention, a vaccine of the type hereinabove described is administered for the purpose of preventing or treating a disease, such as an infection, for example, that caused by a microorganism, such as a bacterium or a virus.

A vaccine in accordance with the present invention may include one or more immunogenic polypeptides or active fragments thereof. When employing more than one polypeptide or active fragment, such as two or more polypeptides and/or active fragments, these may be used as a physical mixture or as a fusion of two or more polypeptides or active fragments to form a larger structure or complex, said larger structure or complex having said component polypeptides or fragments linked together either covalently or by some other chemical means, including electrostatic attraction, and, where covalently linked, said linkage can be in the form of a conventional peptide bond, or may involve some other type of linkage, such as some other type of covalent bond or hydrophobic interaction, possibly involving linkages utilizing non-peptide sequences, such as linkages that are oligomeric or polymeric in nature and not involving subunits composed of ordinary amino acids. Such a fusion fragment or fusion polypeptide may be produced, for example, by recombinant techniques or by the use of appropriate linkers for fusing previously prepared polypeptides or active fragments.

In many cases, the variation in the polypeptide or active fragment is a conservative amino acid substitution, although other substitutions are within the scope of the invention.

In accordance with the present invention, a polypeptide variant includes variants in which one or more amino acids are substituted and/or deleted and/or inserted.

The vaccines finding use in the methods of the present invention also include polynucleotides, either DNA or RNA, either single, double or triple stranded, including immunogenically active fragments, segments and portions thereof.

In another aspect, the invention relates to passive immunity vaccines formulated from antibodies against a polypeptide or active fragment of a polypeptide of the present invention. Such passive immunity vaccines can be utilized, for example, to prevent and/or treat pneumococcal infections in patients. In this manner, according to a further aspect of the invention, a vaccine can be produced from a synthetic or recombinant polypeptide or an antibody against such polypeptide. Thus, the vaccine, or vaccine composition, may be composed of, or may contain in addition to other antigenic structures, one or more antibodies that are then primed by the introduction of an additional antibody, such as where the latter is introduced prior to the vaccine, or vaccine composition.

Still another aspect the present invention relates to a method of using one or more antibodies (monoclonal or polyclonal, natural or recombinant, and regardless of how prepared, i.e., by purification from a natural source, or generated by cloning or by direct chemical synthesis), preferably, but not necessarily, specific for one or more antigenic determinants present in the vaccine, or vaccine composition selected for use in the methods of the present invention.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutically acceptable carriers, diluents and excipients are generally added that are compatible with the active ingredients and acceptable for pharmaceutical use.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N. J. current edition).

Vaccine compositions may further incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art, or for administration through nasal or respiratory routes.

The amount of vaccine sufficient to confer immunity to pathogenic bacteria, viruses, or other microbes is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 0.5 to 500 $\mu$g purified protein may be given. As useful in the present invention, such dosages are commonly sufficient to provide about 1 $\mu$g, possibly 10 $\mu$g, even 50 $\mu$g, and as much as 100 $\mu$g, up to 500 $\mu$g of immunogenic protein, or immunogenic polypeptide, or immunogenically active fragments thereof. In addition, more than one such active material may be present in the vaccine. Thus, more than one antigenic structure may be used in formulating the vaccine, or vaccine composition to use in the methods disclosed herein. This may include two or more individually immunogenic proteins or polypeptides, proteins or polypeptides showing immunogenic activity only when in combination, either quantitatively equal in their respective concentrations or formulated to be present in some ratio, either definite or indefinite. Thus, a vaccine composition for use in the processes disclosed herein may include one or more immunogenic proteins, one or more immunogenic polypeptides, and/or one or more immunogenically active immunogens comprising antigenic fragments of said immunogenic proteins and polypeptides, the latter fragments being present in any proportions selected by the use of the present invention. The exact components, and their respective quantities, making up the vaccines, and vaccine compositions, useful in the methods of the present invention are determined, inter alia, by the nature of the disease to be treated or prevented, the severity of such condition where it already exists, the age, sex, and general health of the recipient, as well the personal and professional experience and inclinations of the researcher and/or clinician utilizing these methods.

The vaccines, or vaccine compositions, useful in the methods disclosed herein are thus enhanced in their immunogenic activity by co-treatment with one or more antibodies, related or unrelated to the antigenic determinants present in the vaccine composition. Such enhanced activity, or potentiation, or priming may take any conceivable immunological form of reaction. Thus, such enhancement may comprise any increased, and beneficial, activity of the immune system resulting from co-treatment of the subject with both vaccine, or vaccine composition, and with an antibody as disclosed herein. Such enhanced immunological activity thus comprises an enhancement of any aspect of immune function, including, but not limited to, any of the protective functions of the immune system of an animal, such as resistance to infection by a pathogen, including bacteria, viruses, fungi, rickettsia, mycoplasma, and parasites, regardless of the type of organisms or the etiology of the underlying disease. Other protective functions of the immune system that may be affected by the methods disclosed herein, and thus may realize an enhancement, are the other immune functions that are stimulated by use of vaccines, or vaccine compositions. Thus, for example, vaccines that may become available for use against various forms of cancers may likewise be enhanced by priming with antibodies as disclosed herein. Thus. specific resistance can be augmented by use of immunopotentiators in conjunction with some form of antigen as in a vaccine employing, for example, attenuated viruses, or even cancer cells. Further, such applications can be used not only to induce resistance but also to induce tolerance, such as where antigens are used in allergy or possibly even an auto-immune disease.

Use of the methods of the present invention may thus be either therapeutic or prophylactic in nature. Further, the methods disclosed according to the present invention may have unique value to special groups of individuals, such as the elderly and children, where use of large amounts of vaccines may be dangerous or ill advised. Here, through priming with antibody, smaller amounts of vaccines may be required to produce an effect in the same range as that seen with much larger doses, thereby avoiding unwanted side effects or overreaction to the immunogenic nature of the vaccines being administered. Of course, in such groups as the elderly, conditions such as infection, auto-immunity, and cancer are more common.

As already described, the timing, dosage and route of administration of the vaccines, or vaccine compositions, as well as the antibodies useful in the present invention are subject to wide variation yet may be critical in determining whether the resulting response thereto is to be positive or negative. Thus, the methods disclosed herein may be capable of inhibiting immune responses as easily as enhancing them given the right set of conditions. Consequently, the priming procedures described herein may, with judicious alteration, be used for immunosuppressive action as well as enhancement. The former may realize some value when applied against allergy, auto-immunity and transplantation.

The immunoenhancement, or priming, resulting from the methods disclosed herein may also affect other aspects of the immune system. Thus, they may produce an enhancement of either the humoral or the cellular response, they may stimulate the action of T lymphocytes, since the latter have surface receptors keenly sensitive to antigenic fragments making up some of the vaccines, or vaccine compositions, useful in the present invention, with the priming being triggered by prior introduction of antibodies as disclosed herein. Thus, Immune responses orchestrated by T-lymphocytes provide a model for the priming effect forming the basis of the present invention in that the actions of such T lymphocytes, together with antigen presenting cells and major histocompatibility complex (MHC), show the value of co-stimulation as a means of realizing immune function.

Regardless of the mechanism of action of the methods disclosed herein, it is clear that the present invention provides a unique means for the treatment of diseases where there is a defect in the immune system and/or an ineffective host defense mechanism, or to enhance activity of the immune system above normal levels.

Thus, the methods disclosed herein also find use in the treatment of animals showing various types of immunodeficiency, wherein said animal, such as a human patient, has a deficient or defective immune system. This condition can takes the form of inadequate production of antibodies by the B lymphocytes when presented with foreign antigens as well as a decreased ability to produced T lymphocytes for mounting of a cellular defense. Thus, the methods disclosed herein have the effect of ameliorating such conditions by priming the immune response elicited by the vaccines, or vaccine compositions, use herein when coupled with the effects or prior administration of one or more antibodies, often specific for the antigenic target of the vaccination procedure, such as an invading pathogen. Thus, the methods of the present invention can partly make up for the presence of immunodeficiency by providing a source of antibody for treatment or prevention of a particular disease condition.

In applying the methods of the present invention, it is necessary to provide an effective amount of the vaccines, or vaccine compositions, used therein. By an "effective amount" is meant the amount of the vaccine, or vaccine composition, that will produce a protective immunogenic effect when coupled with prior administration, or co-administration, of an antibody. It should be noted that the vaccine compositions useful in the methods of the present invention may themselves contain an antibody but that said antibody, if present, is considered separate from the "priming" antibody essential to the methods disclosed herein. Thus, the antibodies used in the present invention have the effect of priming the vaccine, or vaccine composition, regardless of the make-up of said vaccine, or vaccine composition.

A further important component of the methods of the present invention is the use of a "priming" step, comprising administration of one or more antibodies to an animal, especially a human patient, prior to, along with, or just after the administration of a vaccine, or vaccine composition. Because the immune response normally elicited by the administration of a vaccine, or vaccine composition, will commonly require a period of time, or lag period, before the immune response has reached effective levels, the antibody priming step may be employed even up until just after administration of the vaccine, or vaccine composition. Such administration can thus occur at any time up until just after administration of the vaccine, or vaccine composition, and certainly at the time periods already provided above, even as much as a week prior to vaccine administration. Furthermore, the administration of the priming antibody, or antibodies, within the methods of the present invention need in no way be limited to administration of a single antibody, nor be limited to just one administration of one or more such priming antibodies. Thus, the priming antibodies, as used herein, may include any form of antibody, including, but not limited to, monoclonal, polyclonal, recombinant, wholly synthetic, grafted, chimeric, bispecific, single chain, heavy chain, light chain, dimeric, tetrameric, and any active fragments of any of these, such as Fab fragments.

In one embodiment of the present invention, the antibody, or antibodies, used for the priming step (step (a) in the procedure described above) will exhibit specificity toward one or more, but at least one, antigenic determinant present in the vaccines, or vaccine compositions, useful in practicing the invention. However, depending on the mechanism of priming, such as by the stimulation of lymphokines or other cytokines, or other wholly different chemical agents, or by whatever means, the present invention can readily be practiced using antibodies whose specificity is wholly different from that of the antigenic determinants present in the vaccine, or vaccine composition, whose immunogenic activity is to be increased.

In addition, the antibodies useful in practicing the present invention need not necessarily have any effect on the immunogenic activity of the vaccines, or vaccine compositions, useful for the present invention. Instead, the antibodies useful in practicing the invention, and the vaccines, or vaccine compositions, useful in practicing the invention may, when given together, or in some other temporal sequence, have a synergistic effect, such that the sum of the immunological effects of the antibody, or antibodies, and the vaccine, or vaccine composition, when administered separately is less that that realized when the priming process of the present invention is employed.

In accordance with the present invention, the success of the priming effect will depend on the dosage and timing of the administration of the antibody, or antibodies, used to achieve the priming effect. As used herein, the antibody, or antibodies, are commonly administered intravenously, or intramuscularly, or by nasal inhalation, as well as by other convenient routes and are commonly administered in dosages ranging from 5 to 20 mg/kg of body weight of the recipient animal, or from 10 to 20 mg/kg, in some cases about 15 mg/kg of body weight.

A further aspect of the present invention provides for the use of the priming procedure disclosed herein for the treatment and/or prophylaxis of acute and chronic microbial infections.

In accordance with the present invention, such microbial infections commonly include viral infections and bacterial infections. Examples of acute viral infections against which the priming therapy, and prophylaxis, of the present invention finds use includes: respiratory syncytial virus (RSV), herpes viruses, influenza viruses, parainfluenza viruses (PIV), adenoviruses, coxsakie viruses, picorna viruses, rotaviruses, heptatis A virus (HAV), hepatitis B virus (HBV), hepatitis C virus (HCV), hepatitis D virus (HDV), hepatitis E virus (HEV), influenza A virus, and influenza B virus, rubellavirus, measles virus, pox viruses, papilloma viruses, and enteroviruses, arenavirus, rhinoviruses, poliovirus, Newcastle disease virus, rabies virus, arboviruses. The methods of the present invention also find use against recombinant forms of these viruses where such are to be studied in a research setting. For example, the antibodies disclosed in U.S. Pat. No. 5,824,307 are particularly useful for treating respiratory syncytial virus (as well as the asthma and extended periods of wheezing that often persist after infection by this virus).

Of the DNA viruses, those of the herpes group are responsible for many of the viral infections in humans. This viral group includes: herpes simplex virus (HSV), types 1 and 2, varicella zoster virus (VZV), cytomegalovirus (CMV); Epstein-Barr virus (EBV) and human herpes virus 6 (HHV6). HSV 1 and HSV 2 are some of the most common infectious agents of man.

In a specific embodiment of the present invention the priming antibody is an anti-RSV antibody specific for the F antigen of RSV and the vaccine is an anti-RSV vaccine comprising one or more epitopes of the F antigen of RSV (for example, the attenuated RSV vaccine of U.S. Pat. No. 5,993,824 or vaccines containing mutant forms of this organism such as that disclosed in U.S. Pat. No. 5,932,222).

In cases where the methods of the invention are to be employed against bacterial infections, or the prevention thereof, the bacteria will commonly include *E. coli, pneumococcus pneumonii* and *pneumocystis carinii*.

The antibodies, as well as vaccines, useful in practicing the present invention may be administered to a human recipient by a route selected from oral, parenteral (including subcutaneous, intradermal, intramuscular and intravenous), rectal and inhalation. The size of an effective dose of a compound will depend upon a number of factors including the identity of the recipient, the type of immunopotentiation involved, the severity of the condition to be treated and the route of administration, and will ultimately be at the discretion of the attendant physician.

For each of the aforementioned means of administration of antibodies to said patient for the purposes of priming subsequent vaccine administrations, an effective dose of said antibody, or antibodies, will generally be in the range 0.5 to 30 mg/kg bodyweight of the human recipient, on a per daily regimen, preferably in the range 5 to 20 mg/kg bodyweight per day and most preferably in the range 10 to 15 mg/kg bodyweight per day; an optimum dose is 15 mg/kg bodyweight per day, these doses being for human usage only.

The particular dose to be administered may be given as a series of doses, for example, as several sub-doses given over the course of a day, such as between two and four sub-doses administered at appropriate intervals throughout the time course of administration, or may be administered as a single dose, with the number of doses, the dosage of each dose, and the time course depending intimately on the nature of the vaccine, or vaccine composition, the condition of the patient, and the nature of the disease to be either treated or prevented. Thus where three sub-doses are employed each will generally lie in the range 0.1 mg to 10 mg/kg of body weight, preferably 0.5 mg to 5 mg/kg body weight, and most preferably 1 mg to 5 mg/kg bodyweight with an optimum of 5 mg/kg bodyweight. A daily dose for a human weighing of the order of 50 kg will thus generally lie in the range of about 450 mg. Optimally a human daily dose is 450 mg.

In one embodiment, wherein the disease condition to be treated or prevented is respiratory syncytial virus, the treatment may call for a range of about 450 mg as a daily dose, given once a month for a period of about 5 months. The anti-RSV vaccine to be primed in such a procedure would then be administered either at the end of the 5 month period, or could be administered in monthly intervals starting at the time of the second dose of anti-RSV antibody, or some other regimen could be used. Alternatively, administration of the vaccine, or vaccine composition could be carried out simultaneously with each of the antibody administrations, or possibly each of the administrations of vaccine, or vaccine composition, could be given on the day following the administration of antibody, or any other regimen devised by the sound discretion of the clinician after review of the needs of the particular patient as well as considerations of the tolerance of said patient to varying dosages of the vaccine, or vaccine composition, as well as the antibody, or antibodies, to be used.

For an anti-RSV antibody, the desired dose is preferably presented as a single dose, at monthly intervals, over a 5 month period.

It should be reiterated that the process for vaccine priming, as disclosed herein, is a general procedure that can operate to the benefit of any vaccine, or vaccine composition, and employing any antibody. Thus, the antibody use to prime a given vaccine, or vaccine composition, can be selected independently of the particular vaccine, or vaccine composition, and does not have to be an antibody specific for an antigenic determinant of the vaccine. although in such cases the priming effect may work more effectively.

The formulations of the antibodies useful for the processes described herein, include those suitable for parenteral (including subcutaneous, intradermal, intramuscular and intravenous) and nasal or pulmonary administration although the most suitable route may depend upon the age and condition of the recipient. Such formulations may be presented in unit dosage form and may be prepared by any methods well known in the pharmaceutical arts. Of course, all such methods include the condition that the antibodies used, however formulated, maintain their specificity for the antigenic determinants that served as the basis for selection. Thus, because of the polypeptide nature of the antibodies useful in the methods of the invention, any formulation that fails to maintain the overall structural integrity of the antibody protein molecules will likely prove unsuccessful in carrying out the processes according to the present invention. However, formulations known to maintain such structural integrity are well known in the art and include such carriers as saline and glycerol. In general the formulations are prepared by uniformly and intimately bringing into association the active ingredient with liquid carriers or finely divided solid carriers or both.

Formulations for parenteral administration include aqueous and nonaqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Solutions and suspensions suitable for injection may be prepared just prior to use.

Formulations suitable for pulmonary administration via the buccal cavity are presented such that particles containing the active ingredient and desirably having a diameter of under 10 $\mu$m are delivered into the bronchial tree of the recipient.

As one possibility such formulations are in the form of fine powders that may conveniently be presented either in an easily pierced capsule, such as a gelatin, for use in an inhalation device, or alternatively as a formulation comprising active ingredient, a suitable liquid propellant and optionally other ingredients such as surfactant and/or a solid diluent. So-called "self-propelling" formulations of this nature may also be employed wherein the active ingredient is dispensed in the form of droplets of a solution or suspension.

Such formulations are analogous to those well known in the art and may be prepared by established procedures. Such formulations are advantageously presented in a container provided with either a manually-operable or automatically functioning valve having the desired spray characteristics and having some type of valve structure for delivering a metered amount or fixed volume, for example 50 to 100 microliters, upon each operation thereof.

Solutions of the antibodies useful for the methods disclosed herein may also be maintained in the form of a solution for use in an atomiser or nebuliser whereby an accelerated airstream, whether by ultrasonic agitation or some other means, is employed to produce a fine droplet mist for inhalation by the patient. Such methods can also be applied to nasal administration or, for that matter, to any type of introduction of such antibodies via the respiratory system.

More specifically, formulations for nasal administration should have a particle diameter in the range 10 to 200 microns to enable retention in the nasal cavity, often achieved through use of a powder of the proper particle diameters. Of course, dosage levels must be adjusted accordingly.

Preferred unit dosage formulations are those containing an effective dose, as hereinabove recited, or an appropriate fraction thereof, of the active antibody.

The present invention is also directed to a vaccine in which a polypeptide or active fragment thereof is delivered or administered in the form of a polynucleotide encoding the polypeptide or active fragment, whereby the polypeptide or active fragment is produced in vivo. The polynucleotide may be included in a suitable expression vector and combined with a pharmaceutically acceptable carrier.

In addition, polypeptides can be used as immunogens to stimulate the production of antibodies for use in passive immunotherapy, for use as diagnostic reagents, and for use as reagents in other processes such as affinity chromatography.

The present invention also relates to methods of treating or preventing a disease by carrying out the steps described above on an animal at risk of said disease, or afflicted with said disease. Such animal is commonly a human being. Such disease can include that caused by a pathogen, including diseases caused by any and all of the pathogens already enumerated, as well as chronic diseases, such as cancer.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

In practicing the methods disclosed according to the present invention, it should be borne clearly in mind that other and different embodiments of these processes, in addition to those specifically disclosed herein, will no doubt suggest themselves to those of skill in the relevant art.

What is claimed is:

1. A process for priming the immunogenic activity of a vaccine, comprising:

(a) administering to an animal an effective amount of an antibody specific for one or more of the antigenic determinants characteristic of said vaccine which elicits a protective immune response and whose immunogenic activity is to be primed; and (b) administering to said animal an effective amount of the vaccine of step (a) wherein said vaccine comprises at least one antigenic determinant for which the antibody of step (a) is not specific.

2. The process of claim 1 wherein step (a) is carried out at least 24 hours before step (b).

3. The process of claim 1 wherein step (a) is carried out at least 48 hours before step (b).

4. The process of claim 1 wherein step (a) is carried out at least 72 hours before step (b).

5. The process of claim 1 wherein step (a) is carried out at least 1 week before step (b).

6. The process of claim 1 wherein the antibody is specific for more than one antigenic determinant present in the vaccine.

7. The process of claim 1 wherein the effective amount of antibody is in the range of 5 to 20 mg/kg of body weight.

8. The process of claim 7 wherein the effective amount of antibody is in the range of 10 to 20 mg/kg body weight.

9. The process of claim 8 wherein the effective amount of antibody is about 15 mg/kg.

10. The process of claim 1 wherein the effective amount of vaccine is between about 5 $\mu$g per kg of body weight to about 1 gram per kg body weight.

11. The process of claim 10 wherein the effective amount of vaccine is between about 100 $\mu$g per kg of body weight to about 1 gram per kg body weight.

12. The process of claim 10 wherein the amount of vaccine is between about 1 mg per kg of body weight to about 1 gram per kg body weight.

13. The process of claim 10 wherein the effective amount of vaccine is between about 10 mg per kg of body weight to about 1 gram per kg body weight.

* * * * *